(12) United States Patent
Pacetti et al.

(10) Patent No.: US 9,861,508 B2
(45) Date of Patent: Jan. 9, 2018

(54) SHORT PULSE LASER MACHINING OF POLYMERS ENHANCED WITH LIGHT ABSORBERS FOR FABRICATING MEDICAL DEVICES

(71) Applicant: Abbott Cardiovascular Systems Inc., Santa Clara, CA (US)

(72) Inventors: Stephen D. Pacetti, San Jose, CA (US); Joel Harrington, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 15/398,425

(22) Filed: Jan. 4, 2017

(65) Prior Publication Data

US 2017/0112645 A1    Apr. 27, 2017

Related U.S. Application Data

(63) Continuation of application No. 13/802,189, filed on Mar. 13, 2013, now Pat. No. 9,566,666.

(51) Int. Cl.

| | |
|---|---|
| *B23K 26/40* | (2014.01) |
| *A61F 2/915* | (2013.01) |
| *B23K 26/402* | (2014.01) |
| *B29C 35/08* | (2006.01) |
| *B23K 103/00* | (2006.01) |
| *B29K 67/00* | (2006.01) |
| *B29K 105/00* | (2006.01) |
| *B29L 31/00* | (2006.01) |

(52) U.S. Cl.
CPC ............ *A61F 2/915* (2013.01); *B23K 26/402* (2013.01); *B29C 35/0805* (2013.01); *A61F 2002/91558* (2013.01); *A61F 2002/91583* (2013.01); *A61F 2240/001* (2013.01); *B23K 2203/42* (2015.10); *B29C 2035/0838* (2013.01); *B29K 2067/00* (2013.01); *B29K 2105/005* (2013.01); *B29K 2105/258* (2013.01); *B29K 2995/006* (2013.01); *B29L 2031/7532* (2013.01)

(58) Field of Classification Search
CPC ............ A61F 2/915; A61F 2002/91558; A61F 2002/91583; A61F 2240/001; B23K 26/402; B23K 2203/42; B29C 35/0805; B29C 2035/838; B29K 2067/00; B29K 2105/005; B29K 2105/258; B29K 2995/006
USPC ..................................... 219/121.72
See application file for complete search history.

*Primary Examiner* — Brian Jennison
(74) *Attorney, Agent, or Firm* — Squire Patton Boggs (US) LLP

(57) ABSTRACT

A method of laser machining a polymer construct to form a stent that includes a bioresorbable polymer and an absorber that increases absorption of laser energy during laser machining. The laser cuts the tubing at least in part by a multiphoton absorption mechanism and the polymer and absorber have a very low absorbance or are transparent to light at the laser wavelength.

17 Claims, 4 Drawing Sheets

SHORT PULSE LASER MACHINING OF POLYMERS ENHANCED WITH LIGHT ABSORBERS FOR FABRICATING MEDICAL DEVICES

This application is a continuation of U.S. application Ser. No. 13/802,189 filed Mar. 13, 2013 and is incorporated by reference herein.

BACKGROUND OF THE INVENTION

Field of the Invention

This invention relates to laser machining tubing to form stents.

Description of the State of the Art

This invention relates to laser machining of devices such as stents. Laser machining refers to removal of material accomplished through laser and target material interactions. Generally speaking, these processes include laser drilling, laser cutting, and laser grooving, marking or scribing. Laser machining processes transport photon energy into a target material in the form of thermal energy, photochemical energy, or both. Material is removed by melting and blow away, direct vaporization/ablation, or by formation of a plasma with ablation.

When a substrate is laser machined energy is transferred into the substrate. As a result, a region beyond the cutting edge is modified by the energy, which affects the properties in this region. This region may be referred to as the "laser affected zone" (LAZ). In general, the changes in properties in this region are adverse to the proper functioning of a device that is being manufactured. Therefore, it is generally desirable to reduce or eliminate energy transfer beyond removed material, thus reducing or eliminating the extent of modification and size of the region affected.

One of the many medical applications for laser machining includes fabrication of radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Stents have been made of many materials such as metals and polymers, including biodegradable polymeric materials. Biodegradable stents are desirable in many treatment applications in which the presence of a stent in a body may be necessary for a limited period of time until its intended function of, for example, achieving and maintaining vascular patency and/or drug delivery is accomplished. Due to their temporary nature, biodegradable stents are often referred to as scaffolds.

Stents can be fabricated by forming patterns on tubes or sheets using laser machining. Even though the basic laser-material interaction is similar, there are certain aspects that differ among types of materials (such as metals, plastics, glasses, and ceramics), i.e. different absorption characteristics. The properties of biodegradable polymers tend to be very sensitive to energy transfer from laser machining, depending on the laser wavelength and power. It is critical when forming a biodegradable polymer stent from a biodegradable construct using laser machining that damage to the polymer material of the stent pattern from the laser energy is minimized. This requires judicious selection of laser parameters that allow cutting of the polymer in a fast efficient manner while minimizing damage to the polymer.

It has been found that selecting a combination of parameters such as pulse energy, wavelength, and laser pulse duration is critical in defined the optimal process conditions for the type of material. Short pulse lasers can operate in a regime where absorption of energy by the polymer is via a multi-photon process which generates a plasma plume. An advantage of this process is formation of a small or thin LAZ. However, even with the optimal parameters the cutting process can be slower than desired with certain constructs, for example, constructs with thick walls that are used for making peripheral scaffolds. In such situations, modifying the laser parameters to increase cutting speed can result in undesirable damage to the construct material which can adversely affect scaffold performance. In some situations, multiple passes of the laser over the polymer are required to cut completely through leading to long processing times. Therefore, methods are needed for increasing laser machining speed without adversely affecting the material of as fabricated scaffolds.

SUMMARY OF THE INVENTION

Embodiments of the present invention include a method of laser machining a substrate to form a stent, comprising: providing a tube comprising a polymer and an absorber; and laser machining the polymer tube with a laser beam to form a scaffold, wherein the laser beam has a pulse width that provides multiphoton absorption of laser energy from the laser beam, wherein the laser beam has a wavelength such that the extinction coefficient of the polymer at the laser beam wavelength is less than 5% of the extinction coefficient of the polymer at one half the laser beam wavelength, wherein the absorber has a maximum absorbance at a wavelength within 50 nm of one half the laser beam wavelength, and wherein the absorber increases absorption of the laser energy in the tube which allows the laser beam to cut through the wall in one pass of the laser beam using laser cutting speed of 4 to 20 in/min to form the scaffold.

Embodiments of the present invention include a method of laser machining a substrate to form a stent, comprising: providing a tube comprising a poly(L-lactide) (PLLA) and an absorber; and laser machining the polymer tube with a laser beam having a pulse width of 1 to 12 ps and with a laser wavelength of 515 or 532 nm, wherein the absorber has a maximum absorbance in a range between 200 and 300 nm and an extinction coefficient at least 2 times larger than the polymer in the range, and wherein the absorber increases absorption of the laser energy which allows the laser machining to cut through the wall in one pass of the laser beam using a laser cutting speed of 4 to 20 in/min to form a scaffold comprising structural elements.

Embodiments of the present invention include a method of laser machining a substrate to form a stent, comprising: providing a tube comprising a bioresorbable aliphatic polyester polymer and an absorber; and laser machining the polymer tube with a laser beam to form a scaffold, wherein the laser beam has a pulse width that provides multiphoton absorption of laser energy from the laser beam, wherein the polymer is transparent to laser energy at a wavelength of the laser beam, and wherein the absorber has a weight percent extinction coefficient at least 100 times greater than the polymer at one half the wavelength of the laser beam, and wherein the absorber increases ablation of the polymer by the laser beam.

DETAILED DESCRIPTION OF THE INVENTION

Embodiments of the present invention relate to methods of laser machining of polymer constructs to manufacture thick-walled scaffolds such as those for use in peripheral vessels. More specifically, these embodiments relate to increasing the speed of the laser machining of tubing in the fabrications of thick-walled scaffolds. The increase is accomplished by including absorbers in the construct material that increase laser energy absorption in the tubing material without adversely affecting the mechanical, biocompatibility, or absorption properties of the polymer material of the scaffold. The increase in laser energy absorption can be achieved without modifying any laser parameter or any combination of laser parameters such as pulse duration or width, wavelength, or pulse energy.

In general, stents can have virtually any structural pattern that is compatible with a bodily lumen in which it is implanted. Typically, a stent is composed a scaffold including a pattern or network of circumferential rings and longitudinally extending interconnecting structural elements of struts or bar arms. In general, the struts are arranged in patterns, which are designed to contact the lumen walls of a vessel and to maintain vascular patency.

Figure 1:
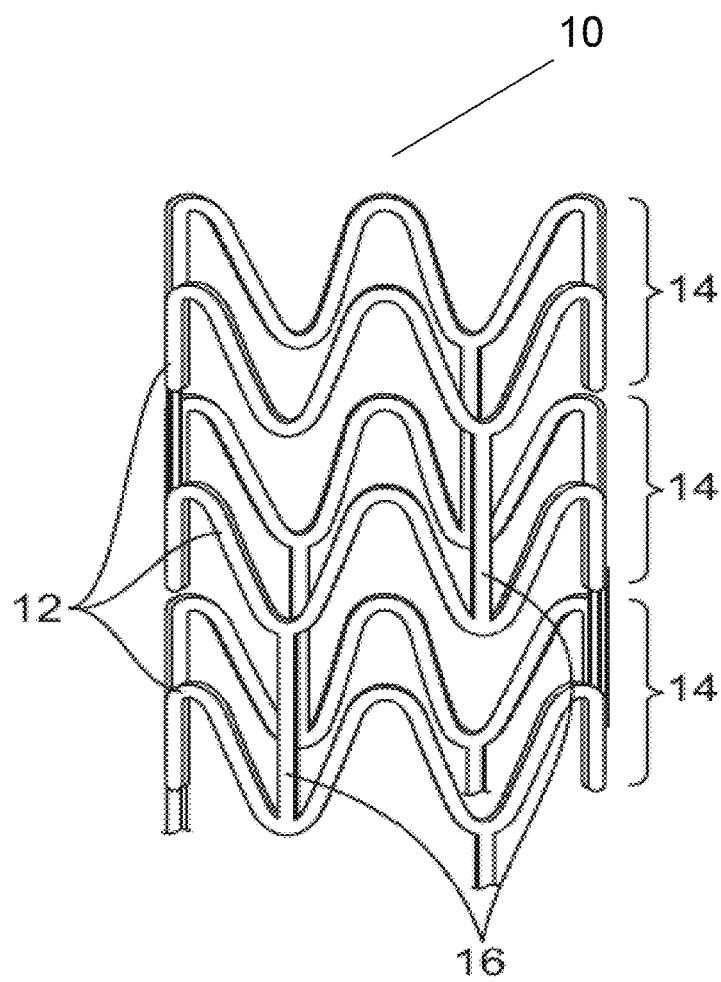
FIG. 1 depicts a stent.

An exemplary structure of a stent is shown in FIG. 1. FIG. 1 depicts a stent 10 which is made up of struts 12 with gaps between the struts. Stent 10 has interconnected cylindrical rings 14 connected by linking struts or links 16. The embodiments disclosed herein are not limited to fabricating stents or to the stent pattern illustrated in FIG. 1. The embodiments are easily applicable to other stent patterns and other devices. The variations in the structure of patterns are virtually unlimited.

A key step in the fabrication of a bioresorbable vascular scaffold is laser machining of the tubing to form the scaffold pattern. A scaffold can be fabricated by laser machining a construct or substrate such as a tube to form the scaffold. Material is removed from selected regions of the construct which results in formation of the structure of the device. In particular, a stent may be fabricated by machining a thin-walled tubular member with a laser. Selected regions of the tubing may be removed by laser machining to obtain a stent with a desired pattern of structural element or struts. Specifically, a laser beam can be scanned over the surface of tubing or the tubing can be translated and rotated under the beam resulting in removal of a trench or kerf extending all the way through a wall of the tubing. When a starting and ending point of a kerf meet, the region surrounded by the kerf drops out or is removed by an assisting gas which creates a gap in the tube wall.

Figure 2:
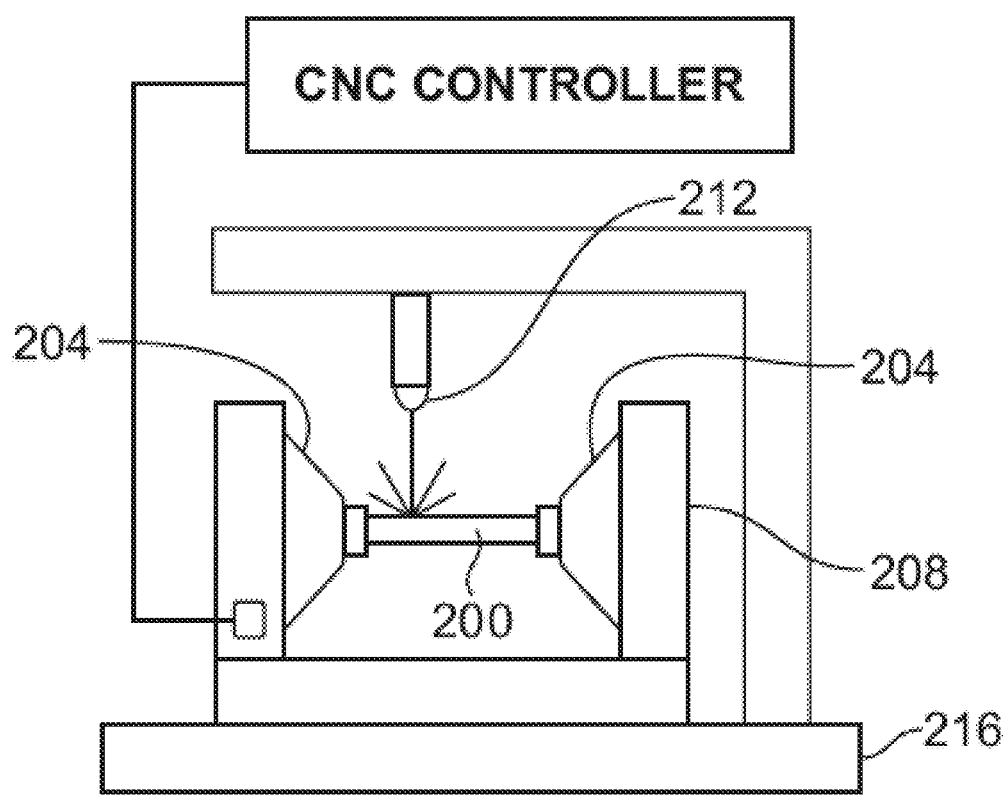
FIG. 2 depicts a machine-controlled system for laser machining a tube.

FIG. 2 depicts an embodiment of a portion of a machine-controlled system for laser machining a tube. Prior to laser machining, the wall of the tube can be free of any holes or gaps. In FIG. 2, a tube 200 is disposed in a rotatable collet fixture 204 of a machine-controlled apparatus 208 for positioning tube 200 relative to a laser 212. According to machine-encoded instructions, tube 200 is rotated and moved axially relative to laser 212 which is also machine-controlled. The laser selectively removes the material from the tubing resulting in a pattern cut into the tube. The tube is therefore cut into the discrete pattern of the finished stent.

Figure 3:
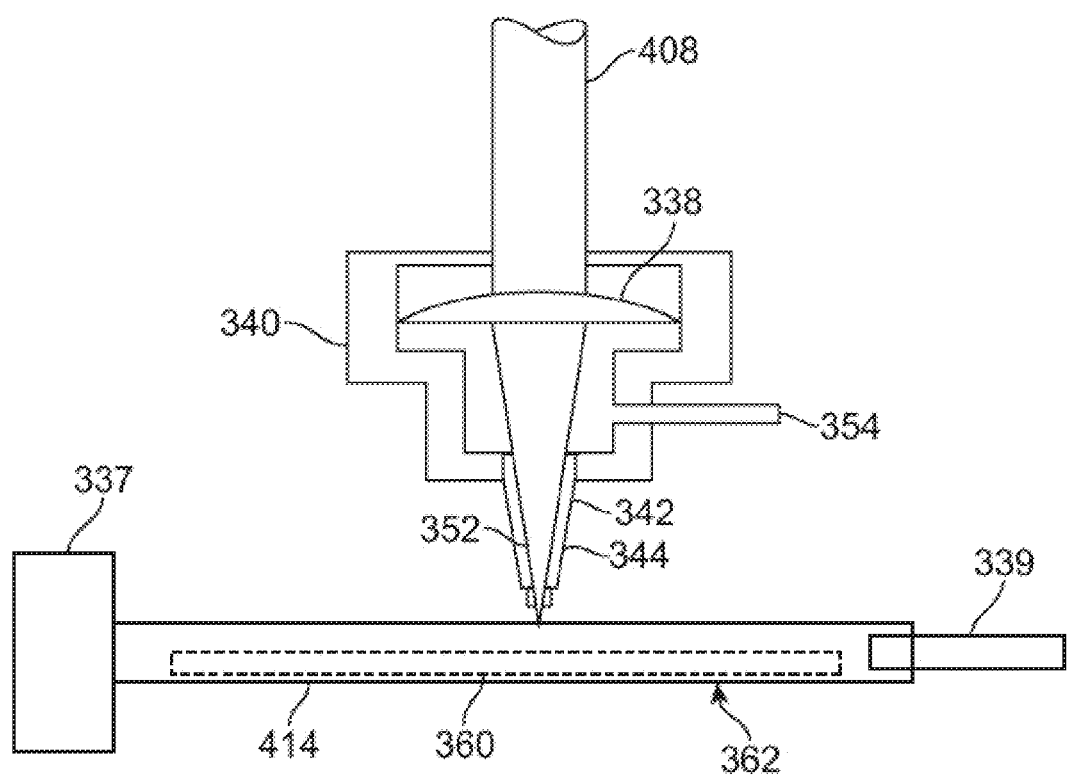
FIG. 3 depicts a close-up axial view of a region where a laser beam interacts with a tube.

FIG. 3 depicts a close-up view of a laser beam 408 interacting with a tube 414. Laser beam 408 is focused by a focusing lens 338 on tube 414. Tube 414 is supported by a controlled rotary collet 337 at one end and an optional tube support pin 339 at another end. A coaxial gas jet assembly 340 directs a cold gas jet or stream 342 that exits through a nozzle 344 that cools the machined surface as the beam cuts and removes ablated or ionized material. The gas stream also helps to remove debris from the kerf and cool the region near the beam. Gas inlet is shown by an arrow 354. Coaxial gas jet nozzle 344 is centered around a focused beam 352. In some embodiments, the pressure of the supplied cooling gas is between 30 and 150 psi. An exemplary flow rate of the cooling gas is between 2 and 100 scfh, or more narrowly, 2 to 20 scfh, 20 to 50 scfh, 50 to 70 scfh, or 70 to 100 scfh. Exemplary cooling gases or process gases include helium, hydrogen, argon, nitrogen, neon, oxygen, or a mixture of those gases.

Biodegradable or bioresorbable polymers that may be suitable for stent scaffold applications include semi-crystalline polymers. In particular, these include polymers with a glass transition temperature (Tg) above human body temperature, which is about 37° C. The polymer substrate or scaffold can be made in whole or in part from a single or a combination of biodegradable polymers including, but not limited to, poly(L-lactide) (PLLA), polymandelide (PM), poly(caprolactone), poly(L-lactide-co-caprolactone), poly (D,L-lactide) (PDLLA), poly(D,L-lactide-co-caprolactone), polyglycolide (PGA), poly(glycolide-co-caprolactone), poly (L-lactide-co-glycolide) (PLGA), and poly(D,L-lactide-co-glycolide) (PDLGA). PLGA or PDLGA may include copolymers containing different molar ratios of units derived from L-lactide or D,L-lactide and glycolide, such as, 90:10, 75:25, 50:50, 25:75, 10:90, or any composition in between.

Several properties of a scaffold are essential for performing its function including, high radial strength to provide mechanical support to a vessel and resistance to fracture. Fracture of a scaffold can occur during crimping, during deployment, and after deployment in a vessel. Fracture can lead to a loss of radial strength, increase acute thrombogenicity, create vessel trauma, generate an embolic hazard and/or potentially cause premature catastrophic failure of the scaffold. Prior to laser machining, the tube may be subjected to processing which enhances radial strength and fracture resistance. Therefore, it is essential that the mechanical properties of the tube material be maintained throughout the laser machining process. Localized energy deposition to the tube material during laser cutting can result in modification of the desired microstructural properties or damage to localized regions.

Laser beam machining is one of most advanced non-contact type machining technology used in micro and nano-fabrication to fulfill the need in handling advanced engineering materials, stringent design requirements, intricate shape and unusual size. Laser machining methods which employ short pulse widths in a range of a picosecond=$10^{12}$) ("Picosecond" lasers) and in the range of a femtosecond ($=10^{-15}$) have been found to be promising in minimizing damage in the laser processing of bioabsorbable polymer scaffolds. "Pulse width" or "pulse duration" refers to the duration of an optical pulse versus time. The duration can be defined in more than one way. Specifically, the pulse duration can be defined as the full width at half maximum (FWHM) of the optical power versus time. Picosecond and femtosecond lasers offer unique advantages for the removal of precise amount of materials with minimum thermal or UV damage to the surrounding material. In general, the picosecond lasers have pulse widths between about 1 and 15 ps, 1 and 12 ps, or 1 and 20 ps and the femtosecond lasers have pulse widths between 10 and 800 fs.

The two fundamental mechanisms involved in the laser ablation are believed to be photothermal and photochemical. In the photothermal mechanism the material is ablated by melting and vaporizing, whereas in the photochemical mechanism the photo energy of light is used to break the chemical bonds of the polymer directly. The chemical bonds between atoms and molecules of the substrate are broken resulting in formation of gaseous species which are removed from the substrate.

Laser ablation of material from a substrate can occur by a thermal mechanism, a nonthermal mechanism, or a combination of both. Longer-pulse lasers, for example, remove material from a surface principally through a thermal mechanism. In a thermal mechanism, the laser energy that is absorbed results in a temperature increase at and near the absorption site and material is removed by conventional melting or vaporization. Thermal damage of uncut substrate material can occur due to melting and thermal diffusion into a region or zone of material at the machining edge.

Lasers with femtosecond pulse duration are of particular interest for ablating material as the pulse duration is less than the typical thermalization characteristic time (i.e., time to achieve thermal equilibrium) which is a few picoseconds. Due to a much smaller thermal diffusion depth, femtosecond laser machining may be considered to remove material by a completely or nearly completely nonthermal mechanism. A picosecond laser removes material mostly through a nonthermal mechanism, but also with some degree of thermal mechanism for some materials that is enough to cause some thermal damage to a substrate.

More specifically, the nonthermal mechanism involves optical breakdown in the target material which results in material removal. During optical breakdown of material, a very high free electron density, i.e., plasma, is produced through mechanisms such as multiphoton absorption and avalanche ionization. With optical breakdown, the target material is converted from its initial solid-state directly into fully ionized plasma on a time scale too short for thermal equilibrium to be established with a target material lattice. Therefore, there is negligible heat conduction beyond the region removed.

As described in U.S. Patent Publication Number 20110307050, it has been found that the nonthermal mechanism can also cause damage to the uncut material which arises from photochemical affects that result in voids within the uncut material. However, it has also been recognized that the damage caused by the thermal and nonthermal mechanisms can be reduced or minimized by laser machining at a laser wavelength such that the polymer has an absorption coefficient at the laser wavelength that is substantially less than the maximum absorbance of the polymer.

In the laser machining of the present invention, the polymer of a laser machined construct has a very low or no absorbance at the wavelength of the laser and thus is almost or completely transparent to the laser beam. Energy is absorbed by the construct via a nonthermal mechanism due to the short pulse duration of the laser.

In some embodiments, the absorbance, extinction coefficient, or extinction coefficient based on weight percent of the polymer at the laser wavelength can be less than 1%, less than 5%, less than 10%, less than 20%, 0.1 to 1%, 1% to 5%, 5 to 10%, 10 to 20%, 20 to 40%, or 40 to 60% of the absorbance, extinction coefficient, or extinction coefficient of the polymer at one half the laser wavelength based on weight percent of the polymer. Additionally or alternatively, the laser wavelength may be 100 nm, 200 nm, 300 nm, 400 nm, 100 to 200 nm, 200 to 300 nm, 300 to 400 nm more than the wavelength of maximum absorbance of the polymer.

The extinction coefficient is a measure of how strongly a substance absorbs light at a particular wavelength. For a well-defined, pure molecular species in, for example, a solvent it is usually represented by units of AU-L/mole-cm where:
AU=absorbance unit
L=liter
cm=centimeter (path length)
In the case of a polydisperse material, such as a polymer, the extinction coefficient can be defined in terms of weight percent and have the units of AU/wt %-cm. The extinction coefficient is a function of wavelength.

For example, PLLA can be machined with a short pulse laser at 515 nm wavelength even though PLLA does not absorb appreciably at 515 nm wavelength. In general, bioresorbable polyester polymers are completely transparent to visible wavelengths from 400-800 nm. In a nonthermal mechanism, absorption of the laser light is accomplished via a non-linear optical process that occurs due to the very high intensity of the short pulse laser. In PLLA, the most accessible chromophore is the ester bond, where a "chromophore" refers to a chemical group capable of selective light absorption resulting in the coloration of certain organic compounds. Instead of a single photon being adsorbed, multiphoton adsorption process occurs. Essentially, two 515 nm photons are adsorbed. The energy of two, 515 nm photons is equivalent to a single 258 nm photon and the ester bond in PLLA does absorb minimally at this wavelength.

As described in U.S. Patent Publication Number 20110307050, short pulse laser process parameters can be adjusted and defined for particular polymers to provide a balance between thermal and nonthermal damage that adversely affects mechanical properties of a finished scaffold, such as radial strength, elongation at break, or fracture resistance. The laser parameters that are adjusted include the pulse width, pulse repetition rate, power, and wavelength of the laser energy.

In particular, the extent and depth of the damage caused by the photochemical mechanism can be controlled by laser parameters such as pulse width and wavelength. It is believed that in laser machining polymers, there is a tradeoff between damage caused by a thermal and nonthermal mechanism. Although the character of the damage caused by each mechanism is different, both can adversely affect scaffold performance. The laser parameters (e.g., pulse width and wavelength) can be adjusted to reduce the photochemical effects, but with some increase in the thermal mechanism.

Specifically, with respect to wavelength adjustment, the lower the single-photon absorption coefficient of a polymer at a given range of wavelength, the lower is the thermal effect on the polymer substrate. The photochemical removal increases and thermal side-wall damage decreases as the wavelength changes from a wavelength range of low single-photon absorption by the polymer to high single-photon absorption by the polymer. Additionally high energy photons (in or near the UV) have the potential to photochemically damage polymer areas around the cut. With respect to pulse width, as the pulse width in the femtosecond or picosecond range decreases, the photochemical removal at a fixed pulse energy increases and the thermal sidewall damage decreases. Parameters can be adjusted by determining a combination of wavelength and pulse width, for example, that minimize adverse photochemical effects such as voids and variation of mechanical properties near the cut sidewall surface as well as minimizing adverse thermal effects such as melting.

For example, laser wavelength found to be advantageous for PLLA is in the visible light spectrum from 390 to 800 nm. More narrowly, the laser wavelength is in the green spectrum or from about 496 to 570 nm, or even more narrowly 532 nm or 515 nm. The pulse width found be advantageous can be 0.8 ps or less, 0.8-1 ps, 1-5 ps, 5-10 ps, 10-12 ps, 12-15 ps, or 15 to 20 ps. A 10 ps laser with 532 nm wavelength at repetition rate of 80 kHz results in minimal damage to the PLLA scaffold as compared to other combinations of wavelengths with lower pulse widths.

Minimizing photochemical damage may correspond to minimizing the thickness of a laser affected zone next to the laser machined edge that includes voids. For example, the thickness of the region can be less than 2 microns, less than 5 microns, less than 20 microns, or less than 30 microns. The void region can be 1-2 microns, 2-5 microns, 2-10 microns, 2-20 microns, or 5-10 microns.

Mechanical properties such as the modulus have been found to vary with distance from a cut surface. Additionally or alternatively, minimizing photochemical damage can help reduce the modulus variation of a cut stent with distance in the laser affected zone. The parameters may be adjusted to obtain faster convergence of the modulus toward a modulus of an undamaged polymer substrate. The modulus may converge at less than 4 microns, less than 8 microns, or less than 20 microns from the machined edge surface. The modulus may converge at between 1-4 microns, 4-8 microns, or 8-20 microns from the machined edge surface. The modulus may converge at 4 microns or less, 8 microns or less, 15 microns or less, or 20 microns or less from the machined edge surface.

The pulse width may be adjusted at a given wavelength to avoid excessive melting, even with an appropriate level of cooling during machining. Excessive melting may correspond to greater than 0.25, 0.5, greater than 1 micron, 0.25 to 0.5 micron, or 0.5 to 1 micron thickness of melted material.

Additional laser parameters are also selected to be used with desired laser wavelength and pulse duration described herein. As described in U.S. Patent Publication Number 20110307050, laser machining a tube to make a coronary scaffold includes selecting the average laser power or power (energy per pulse×repetition rate) and repetition rate for a given pulse width and wavelength to provide a fluence (energy per pulse/spot size of beam) that is high enough so that the beam cuts the substrate all the way through the polymer tubing. The beam spot size is generally is 10 to 20 microns, but can be less than 10 or greater than 20 microns depending on the application. A pulse energy and fluence (based on a 10 micron spot size) for laser cutting polymers can be 4 to 200 µJ and 0.5-200 J/cm2, respectively. The average power per pulse of a beam can be 0.5 to 4 W. More narrowly, the power can be 0.5 to 1 W, 1 to 1.5 W, 1.5 to 1.8 W, 1.8 to 2 W, 2 to 2.2 W, 2.2 to 2.5 W, 2.5 to 2.8 W, 2.8 to 3 W, 3 to 3.2 W, 3.2 to 3.5 W, 3.5 to 3.8 W, 3.8 to 4 W. For a 10 ps pulse width laser, the repetition rate can be 25 to 100 kHz, 25 to 50 kHz, 50 to 60 kHz, 60 to 80 kHz, or 80 to 100 kHz. Exemplary laser parameters for laser machining are additionally are given in Table 1.

Additionally, the repetition rate and cooling gas flow rate (e.g., in SCFH He) are adjusted or selected in combination to reduce or minimize thermal effects (e.g., melting at surface of cut) and to maximize cutting speed. The cutting speed is the scan rate of the laser beam over the surface of a construct or substrate. Exemplary cutting speed is 4 to 20 in/min, or more narrowly, 4 to 8, 8 to 12, or 12 to 20 in/min. These ranges of cutting speed provide an acceptable process time for cutting a coronary or peripheral scaffold.

Bioabsorbable polymer scaffolds for coronary artery treatment can have a length between 8 to 38 m, or more narrowly, between 12 and 18 mm. Such coronary scaffolds may be laser cut from polymer tubes with a diameter between 2.5 mm to 4.5 mm and with a wall thickness of 100-250 microns or more narrowly 100 to 160 microns or 160 to 250 microns. A bioabsorbable polymer scaffold for peripheral treatment, for example, superficial femoral artery (SFA) treatment is typically longer, has a larger diameter, and has thicker struts than a coronary scaffold. For example, the scaffolds may have a length 18 and 38 mm, 38 and 60 mm or even between 60 and 200 mm. An SFA scaffold may be cut from tubing with a diameter of between 5-10 mm, 6-8 mm and a wall thickness of greater than 160 microns, for example, 160 to 250 microns, 180 to 250 microns, 250 to 300 microns, 300 to 350 microns, 350 to 400 microns, or greater than 400 microns.

As described herein, a construct such as a tube can have walls that are too thick for the laser beam with a cutting speed within these ranges and that also has a desired set of parameters including wavelength, pulse width, and laser power to cut all the way through the wall in one pass. The desired set of parameters may be those described herein that reduce or minimized both nonthermal and thermal effects.

In general, the repetition rate and cutting speed are directly proportional, i.e., the faster the repetition rate, the faster the cutting speed, resulting in a lower process time per scaffold. However, as the repetition rate is increased, the thermal effects tend to increase. Thus, the repetition rate may be limited to the ranges disclosed herein in order to keep the thermal effects acceptable.

An increase in the cooling gas flow rate can mitigate the thermal effects from the increased repetition rate, allowing a higher repetition rate, and thus cutting speed. However, the increase in the cooling rate may be insufficient to limit thermal effects.

TABLE 1

Exemplary Laser parameters

| Parameter | Value |
| --- | --- |
| Wavelength, nm | 532 nm or 515 nm |
| Polarization | Circular |
| Average laser power, W | 1.5-3.0 |
| Pulse energy | 21 μJ |
| Pulse width | 12 ps |
| Repetition rate | 80 kHz |
|  | 100 kHz |
| Gas (Helium) Flowrate, SCFH | 6 to 10 |
| Nozzle to substrate distance | 0.9 mm |
| Beam size | 8 mm |
| cutting speed, inch/min | 4 to 16 |

Due to the larger strut thickness, as well as the overall longer lengths of scaffolds, the process times for laser machining a SFA scaffold can be much longer than for a coronary scaffold. Table 2 lists the approximate times to laser cut a coronary scaffold and SFA scaffolds, each made of PLLA.

TABLE 2

Laser Machining Times for Resorbable Coronary and SFA Scaffolds per Pico Laser Head

| Bioresorbable Scaffold | Laser Machining Time (minutes) |
| --- | --- |
| 3.0 × 18 mm (coronary) | 2.3 |
| 6.0 × 60 mm (SFA) | 40 |
| 6.0 × 120 mm (SFA) | 80 (estimated) |

The laser parameters for both types of scaffolds are the same and are based on those derived for the coronary scaffold as described above: wavelength of 515 nm and pulse duration of 6 picoseconds. The strut width of the coronary scaffold is 158 microns and the strut width of the SFA scaffold is 300 microns.

Lasing times for the SFA scaffolds are up to 20 times longer than those for coronary. One reason for this is that that larger strut thickness of the SFA scaffold requires multiple passes (2-3) for the picosecond laser to cut through the PLLA tube. The pulse power is not high enough to cut all the way through the SFA tubing in one pass. A second reason is the overall much larger size of the SFA scaffolds. The slow processing time increases the production cost.

The processing time for the SFA scaffold for the same pulse duration can be increased by increasing the laser power, for example, to the point that the laser beams cut through in one pass so that multiple passes would not be necessary. However, increasing power could result in increased scaffold damage that would adversely affect scaffold performance.

Absorptivity of the bioresorbable polymer such as PLLA is limited by the multi-photon adsorption process which is not efficient. The inventors have found a way to increase the absorption of laser energy of a bioresorbable polymer (e.g., PLLA) at a specified laser wavelength (e.g., 515 nm) without increasing the power of the laser and causing increased scaffold damage and which also allows single pass cutting and faster movement of the PLLA tube under the laser.

Embodiments of the present invention include polymer constructs such as tubing made from compositions composed of biocompatible, absorbing material or absorbers and polymers such as polyester bioresorbable polymers. The absorbers absorb laser energy during laser machining and increase the amount of energy absorbed by composition from the laser.

Embodiments further include methods that provide for faster laser cutting with short pulse lasers that cut the polymer at least in part by a multi-photon absorption process. Such short pulse lasers may have a pulse duration 80 fs to 20 ps, or more narrowly 80 to 100 fs, 100 to 500 fs, 500 fs to 1 ps, 1 to 5 ps, 5 to 10 ps, 10 to 12 ps, or 12 to 20 ps. The absorber in the composition may increase energy absorption sufficient to provide one pass cutting of the scaffold pattern such that the laser beam cuts all the way through the wall of a construct such as a tube in one pass at any of the disclosed laser parameter described herein.

The embodiments are applicable to laser machining any type of polymer construct, such as a tubing of any thickness. However, the increased energy absorption provided by the absorber is particularly critical for laser machining thicker-walled tubes used for fabricating SFA scaffolds. In particular, the polymer tubing can have a thickness greater than 160 microns, greater than 180 microns, or greater than 200 microns. The thickness can be 160 to 200 microns, 200 to 250 microns, 250 to 300 microns, or greater than 300 microns.

A polymer construct, such as a tube, that includes an absorber as described herein may allow one pass cutting using a laser with the desired laser parameters. It is believed that the absorber increases the absorption of laser energy by the construct which is used for ablation. Therefore, the energy deposited into the construct is used more efficiently, i.e., more of the energy deposited is used for ablation. In contrast, it is believed that manipulating laser parameters to increase the amount of energy or energy per unit time deposited into the construct (i.e., wavelength, pulse width, power, repetition rate) may allow higher cutting speed with one pass cutting, however, the energy deposited in not necessarily used more efficiently. It is believed that the increased energy is used for ablation, but also results in increased damaged to the uncut substrate.

The present invention is applicable to laser machining constructs to form scaffolds made from or including any type of polymer, in particular, bioresorbable aliphatic polyesters. Exemplary polymers aside from PLLA include polyglycolide (PGA), poly(4-hydroxybutyrate) (P4HB), polycaprolactone (PCL), poly(trimethylene carbonate) (PTMC), poly(butylene succinate) (PBS), poly(p-dioxanone) (PDO), and copolymers thereof. The copolymers can be random, alternating, or block copolymers. Additional bioresorbable polymers include poly(D-lactide), poly(L-lactide-co-glycolide), poly(L-lactide-co-D,L-lactide), poly(glycolide-co-caprolactone), poly(D,L-lactide-co-caprolactone), poly(L-lactide-co-glycolide) (PLGA), and poly(D,L-lactide-co-glycolide) (PDLGA). The PLGA or PDLGA includes those having a mole % of (LA or DLA:GA) of 85:15 (or a range of 82:18 to 88:12), 95:5 (or a range of 93:7 to 97:3), or commercially available PLGA or PDLGA products identified being 85:15 or 95:5 PLGA or PDLGA.

In general, the absorbers do not absorb appreciably at the wavelength, $\lambda$, of the short pulse laser. In some embodiments, the absorber has no absorbance or is transparent at the wavelength, $\lambda$, of the short pulse laser. However, the absorber may have appreciable absorbance at $\lambda/2$.

In some embodiments, the absorber may have its maximum absorbance at a wavelength within a range of $\lambda/2 \pm 100$ nm; within a range of $\lambda/2 \pm 50$ nm; within a range of $\lambda/2 \pm 20$ nm; within a range of $\lambda/2 \pm 10$ nm; within a range of $\lambda/2 \pm 5$ nm; or within a range of $\lambda/2 \pm 1$ nm, where "range of $\lambda/2 \pm 100$ nm," for example, can refer to a range $\lambda/2 + 100$ nm, $\lambda/2 - 100$ nm, or both.

Alternatively or additionally, the absorber may have its maximum absorbance at a wavelength within a range of $\lambda/2 \pm 100$ nm; within a range of $\lambda/2 \pm 50$ nm; within a range of $\lambda/2 \pm 20$ nm; within a range of $\lambda/2 \pm 10$ nm; within a range of $\lambda/2 \pm 5$ nm; or within a range of $\lambda/2 \pm 1$ nm of the maximum absorbance of the polymer of the construct.

In some embodiments, the absorbers are completely transparent or have no absorbance at the wavelength of the laser. Alternatively or additionally, the extinction coefficient or weight percent extinction coefficient of the absorber may be at least 2, 5, 10, 20, 100, 1000, 10,000, and 100,000 times larger at $\lambda/2$ than at $\lambda$. Alternatively or additionally, the extinction coefficient or extinction coefficient weight percent of the absorber may be at least 2 to 5, 5 to 10, 10 to 20, 20 to 100, 100 to 1000, 1000 to 10,000, or 10,000 to 100,000 larger at $\lambda/2$ than at $\lambda$.

Alternatively or additionally, the extinction coefficient or weight percent extinction coefficient of the absorber may be at least 2, 5, 10, 20, 100, 1000, 10,000, or 100,000 times larger at $\lambda/2$ than the polymer of the construct at $\lambda/2$. Alternatively or additionally, the extinction coefficient or weight percent extinction coefficient of the absorber may be at least 2 to 5, 5 to 10, 10 to 20, 20 to 100, 100 to 1000, 1000 to 10,000, or 10,000 to 100,000 larger at $\lambda/2$ than the polymer of the construct at $\lambda/2$.

In exemplary embodiments, the laser has a pulse with of 6 to 15 ps and a wavelength of 515 nm. In these embodiments, absorbers useful for laser machining aliphatic polyesters such as PLLA may have strong absorption in the Ultraviolet (UV) range or in the range of 200 to 400 nm. Specifically, the absorber may have its maximum absorbance at a wavelength (lambda max) and/or have at least some absorbance of laser light within 100 nm, 50 nm, 20 nm, 10 nm, 5 nm, or 1 nm of $\lambda/2$ or 258 nm. Alternatively or additionally, the absorber may have at least some absorbance of laser light within 100, 50, 20, or 10 nm of $\lambda/2$ or 258 nm. Alternatively or additionally, the extinction coefficient of the absorber may be at least 5, 10, or 20 times larger at $\lambda/2$ or 258 nm than at $\lambda$.

The polymer tubing including the absorber can be formed by mixing the absorber in powder or liquid form with the polymer in an extruder during the tube formation process. The absorber can be metered into the resin hopper on the extruder. The absorber should be temperature stable so it will not degrade or deteriorate from the extrusion process necessary to form the polymer tube. For example, the extrusion temperature of PLLA is greater than 173 deg C., greater than 200 deg C., 180 to 200 deg C., 180 to 220 deg C. The absorber should also possess high biocompatibility since it will be released when the polymer bioresorbs in the body. The absorber may be dispersed uniformly throughout the polymer construct.

In some embodiments, the absorber has a melting point lower than the extrusion temperature. Thus, the absorber melts during extrusion and is dispersed throughout the polymer.

Additionally, it is desirable that the absorber content in the tubing or scaffold be low enough that the mechanical properties of the scaffold are not adversely affected. Therefore, it is desirable that the absorbance increase to the construct per unit weight of the absorber in the construct be as high as possible. In some embodiments, the content of the absorber in the tubing is less than 0.001 wt %, less than 0.01 wt %, less than 0.1 wt %, 0.001 to 1 wt %, 0.001 to 0.01 wt %, 0.01 to 0.1 wt %, or 0.001 to 0.1 wt %. A polymer construct composed of a polymer may have an absorber content in any of the above disclosed ranges that also has any of the disclosed absorber properties or ranges disclosed herein.

Absorbers that include a phenyl ring in their structure may be used with lasers with a wavelength in the green spectrum or from about 496 to 570 nm, or even more narrowly 532 nm or 515 nm since the phenyl ring absorbs in the UV range. Exemplary absorbers with phenyl rings for a bioresorbable polymer that are strong absorbers in the UV range include butylated hydroxytoluene (BHT) and methyl paraben.

BHT, which is shown below, is an anti-oxidant free radical scavenger currently present in everolimus to protect it from degradation. BHT is widely used as an anti-oxidant in drugs and foodstuffs.

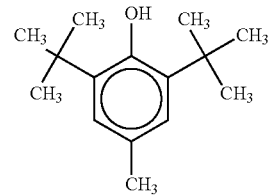

Methyl Paraben, shown below, is an antimicrobial and antifungal agent which occurs naturally in blueberries. Methyl paraben is used widely in parenteral drugs as a preservative. Consequently, it is a substance that is currently administered directly into the bloodstream.

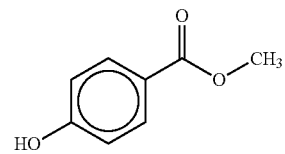

The effectiveness of BHT and methyl paraben as absorbers in PLLA for laser machining with a laser with a wavelength of 515 nm was considered. UV-visible spectra was collected on four types of samples, two PLLA tubing samples, BHT, and methyl paraben. The tubing samples were prepared from two different sources of PLLA. The PLLA tubing was made by extrusion and then was radial expanded to a larger diameter using blow molding at a temperature above the Tg of PLLA.

One tubing sample was prepared from PLLA obtained from PURAC, Lincolnshire, Ill., Lot 10805N5, XLHRSA2075771-01. The other tubing sample was prepared from PLLA obtained from Evonik, Birmingham, Ala., Lot 20228N5, XLHRSA2075771-03.

The UV-vis spectra was collected in dichloromethane ($CH_2Cl_2$) as it is a good solvent for these compounds, including PLLA, and has a UV cutoff at a low wavelength of 233 nm. The UV cutoff of a solvent is the wavelength at which the solvent absorbance in a 1 cm path length cell is equal to 1 AU (absorbance unit) using water in the reference cell. A solvent for studying the absorbance of a substance should be both a good solvent for the substance and have a UV cutoff below that of the substance since the substance in the solvent is not visible below that of the UV cutoff of the solvent.

Figure 4:
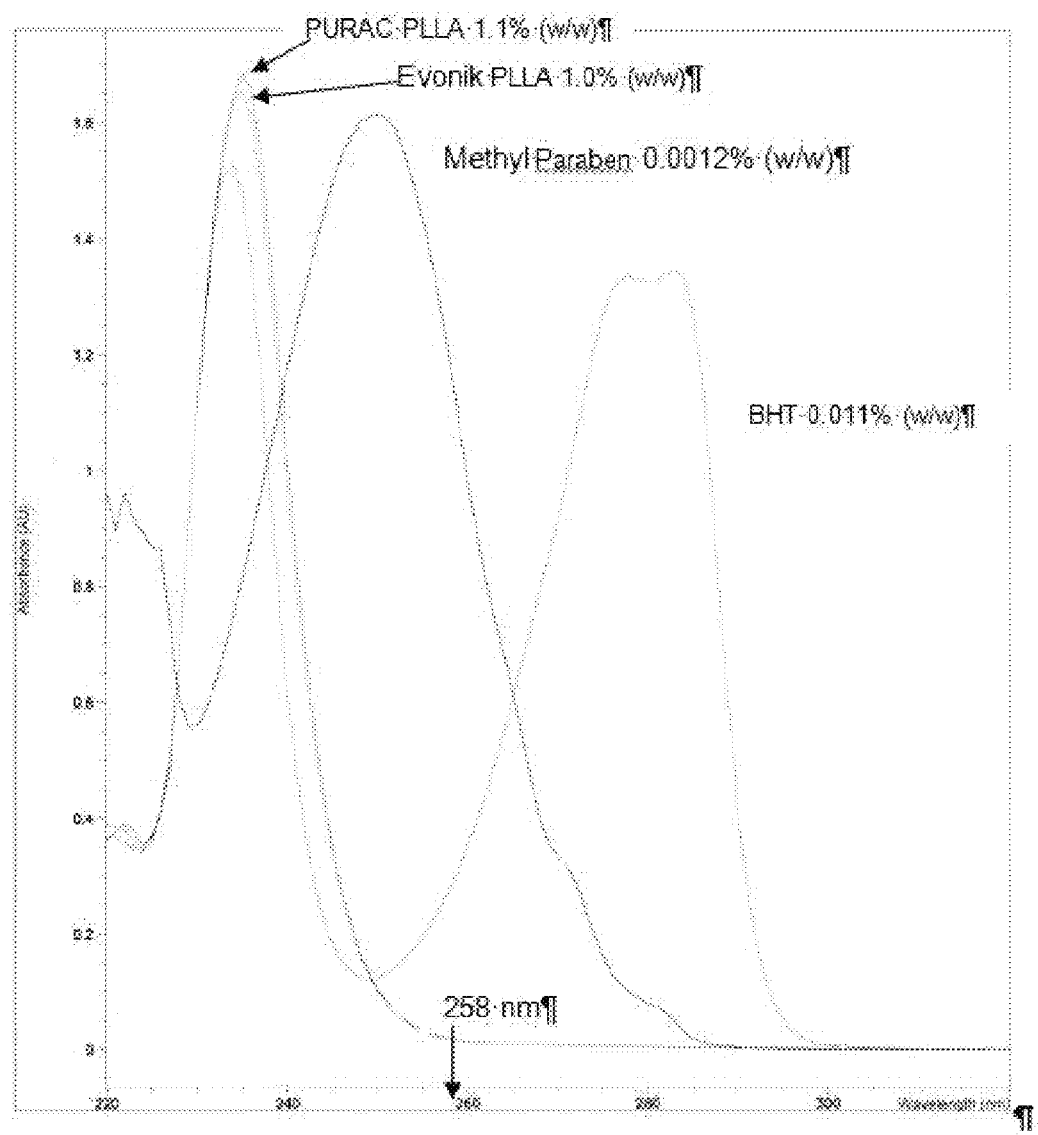
FIG. 4 depicts the absorbance as a function of wavelength of the laser for samples of polymers and absorbers.

FIG. 4 depicts the absorbance as a function of wavelength of the laser for each sample. Table 3 includes the lambda max and weight percent extinction coefficients in $CH_2Cl_2$ at $\lambda/2$ or 258 nm for the four samples. Lambda Max is the wavelength of maximum absorption.

TABLE 3

Lambda Max and Weight Extinction Coefficients at 258 nm.

| Substance | Lambda Max (nm) | Weight Percent Extinction Coefficient at 258 nm (units AU/cm-wt %) |
|---|---|---|
| PURAC PLLA | 230-235 | $1.64 \times 10^{-2}$ |
| Evonik PLLA | 230-235 | $1.56 \times 10^{-2}$ |
| BHT | 234, 281 (two peaks) | 26.3 |
| Methyl Paraben | 250 | 991 |

Weight percent extinction coefficient is defined by the equation: $A = \epsilon\% \, b \, wt\%$ where A=absorbance in AU
$\epsilon\%$=weight percent extinction coefficient
b=optical path length (cm)
wt %=wt % of solute in solution or matrix.

The PLLA from both vendors has a low absorbance at $\lambda/2$ or 258 nm. In some cases, differences in how the expanded PLLA tubing is laser cut were observed. That is some lots of tubing cut easier than others, i.e., at a given laser power, the laser cuts through the tube wall faster. One mechanism for this may be a differing UV absorbance between lots of PLLA expanded tubing. It is believed that different levels of stannous octoate in the expanded tubing may change the resin UV absorbance, and consequently, change the laser cutting. Stannous octoate is a yellow compound which absorbs in the UV. Stannous octoate is a catalyst used in the polymerization to synthesize PLLA from monomer. The tubes may, therefore, contain residual stannous octoate.

Compared to PLLA, both BHT and methyl paraben absorb much more strongly in the UV. FIG. 4 shows the UV spectra overlaid for these four substances. BHT and especially methyl paraben are much stronger absorbers at $\lambda/2$ or 258 nm than PLLA from either vendor. For the listed concentrations in weight percent, at $\lambda/2$ or 258 nm, the absorbance of PLLA is about 0.02 AU while the absorbance of methyl paraben is about 1.1 AU and the absorbance of BHT is about 0.3 AU. The weak absorbance of PLLA at $\lambda/2$ or 258 nm is due to the ester bond energy absorbance which has a maximum absorbance at a much shorter wavelength, 230-235 nm.

The high absorbance of BHT and methyl paraben at $\lambda/2$ or 258 nm shown in FIG. 4 indicates that only a small amount of BHT or methyl paraben is needed to be added to the PLLA to greatly enhance the UV absorbance of PLLA tubing. Table 3 lists the quantities of BHT or methyl paraben that may be added to PLLA to increase the UV absorbance two times and ten times at $\lambda/2$ or 258 nm. It is expected that these small amounts of added UV absorber will not alter the mechanical properties of the PLLA or affect its degradation properties. BHT and methyl paraben are small molecules that will be released from the PLLA as it resorbs.

TABLE 3

Percent Weight Loading Needed to Increase PLLA UV Absorbance

| Substance | Weight Percent in PLLA Needed to Double the 258 nm Absorbance | Weight Percent in PLLA Needed to Increase the 258 nm Absorbance 10X |
|---|---|---|
| BHT | 0.06 | 0.6 |
| Methyl Paraben | 0.0016 | 0.016 |

Additional absorbers that have strong UV absorbance, include a phenyl ring, and are biocompatible include sodium benzoate, benzoic acid, benzyl alcohol, phenoxyl alcohol, gentisic acid, butylated hydroxyl anisole, ethyl benzoate, methyl gallate, ethyl gallate, propyl gallate, ethyl paraben, propyl paraben, benzyl benzoate, resveratrol, alpha tocopherol.

All of these compounds have at least one phenyl ring which is responsible for their strong UV absorbance. Additionally, all of these compounds have a history of use in intravenous or parenteral drugs, are found naturally in the body, or are approved for use in foodstuffs. The compounds are at least as chemically stable as PLLA, with a few being even more thermally stable.

Additionally, inorganic or metal based substances may be used as the UV absorbers. The metal ions of tin, iron, magnesium, and zinc are biocompatible. Metallic or inorganic UV absorbers may include stannous octoate, stannous fluoride, ferrous hydroxide, ferrous fumarate, ferrous gluconate, ferrous sulphate, magnesium carbonate, magnesium citrate, magnesium gluconate, magnesium oxide, magnesium hydroxide, magnesium phosphate, magnesium salicylate, magnesium sulphate, magnesium trisilicate, zinc acetate, zinc carbonate, zinc gluconate, zinc oxide, zinc stearate, zinc sulphate, zinc sulphide, and zinc undecylenate.

In some embodiments, the construct is free of absorbers that absorb strongly at the laser wavelength, for example, absorbers that have a wavelength of maximum absorption within 20 nm, 30 nm, or 10 nm of the laser wavelength are excluded. For example, visible dyes may be excluded. In some embodiments, the absorbers are completely transparent at the laser wavelength.

For machining a PLLA substrate, the absorbers may include only substances that absorb light at wavelengths less than 400 nm when used with short pulse lasers in the picosecond to femtosecond ranges disclosed herein, and that emit light at wavelengths greater than 400 nm.

In further embodiments, drugs or therapeutic agents that absorb strongly in the UV range may be used as absorbers. Exemplary drugs that are strong UV absorbers include salicylic acid, acetyl salicylic acid (aspirin), dexamethasone, dexamethasone acetate, momentasone, clobetasol furoate, and prednisone.

Embodiments of the invention further include a tube or construct prior to laser machining that includes the polymer and the absorber at any of the contents described herein. The embodiments further include a scaffold after laser machining including the polymer and the absorber at any of the contents described herein. The scaffold can further have the disclosed limited damage such as voids and variation in mechanical properties disclosed herein.

The following definitions apply herein:

All ranges include the endpoints and any value within the endpoints, unless otherwise specified.

Polymers can be biostable, bioabsorbable, biodegradable, bioresorbable, or bioerodable. Biostable refers to polymers that are not biodegradable. The terms biodegradable, bioabsorbable, bioresorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body.

"Radial strength" of a stent is defined as the minimum pressure at which a stent experiences irrecoverable deformation.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

The "maximum load" or ultimate load is the absolute maximum load (force) that a structure can bear without failing.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus is the initial slope of a stress-strain curve, and therefore, determined by the linear Hookean region of the curve. For example, a material has both a tensile and a compressive modulus.

"Strain" refers to the amount of elongation or compression that occurs in a material at a given stress or load.

"Elongation" may be defined as the increase in length in a material which occurs when subjected to stress. It is typically expressed as a percentage of the original length.

"Elongation to Break" is the strain on a sample when it breaks. It is usually is expressed as a percent.

The "glass transition temperature," Tg, is the temperature at which the amorphous domains of a polymer change from a brittle, glassy vitreous state to a solid deformable, rubbery or ductile state at atmospheric pressure. In other words, the Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of laser machining a substrate to form a stent, comprising:
   providing a polymer tube comprising a mixture of a polymer with an absorber for increasing the amount of energy absorbed by the tube from a laser; and
   laser machining the polymer tube with a laser beam to form a scaffold, wherein the laser beam has a wavelength ($\lambda$) and a pulse width that provides multiphoton absorption of laser energy by the tube at $\lambda/2$,
   wherein the absorber has a maximum absorbance within 50 nm of $\lambda/2$ and the absorber has an extinction coefficient or weight percent extinction coefficient at least 5 times larger at $\lambda/2$ than at $\lambda$ and at least 5 times larger at $\lambda/2$ than that of the polymer which provides increased absorption of the laser energy by the tube and increased ablation of the tube resulting in faster laser cutting of the tube without an increase in power of the laser.

2. The method of claim 1, wherein the absorber is transparent to the laser beam $\lambda$.

3. The method of claim 1, wherein the polymer is an aliphatic polyester polymer.

4. The method of claim 1, wherein the extinction coefficient of the polymer at $\lambda$ is less than 5% of the extinction coefficient of the polymer at $\lambda/2$.

5. The method of claim 1, wherein a content of the absorber in the tube is 0.001 to 0.1 wt %.

6. The method of claim 1, wherein the pulse width is 80 fs to 20 ps.

7. The method of claim 1, wherein the absorbance of the tube at $\lambda/2$ is at least 2 to 10 times the absorbance of the tube without the absorber.

8. The method of claim 1, wherein the absorber comprises a compound including a phenyl ring.

9. The method of claim 1, wherein the absorber comprises butylated hydroxytoluene (BHT) or methyl paraben.

10. The method of claim 1, wherein the polymer is poly(L-lactide).

11. The method of claim 1, wherein the absorber comprises metallic or inorganic compounds.

12. A method of laser machining a substrate to form a stent, comprising:
    providing a tube comprising a mixture of poly(L-lactide) (PLLA) and an absorber for increasing the amount of energy absorbed by the tube from a laser; and
    laser machining the polymer tube with a laser beam having a pulse width of 1 to 12 ps and with a laser wavelength of 515 or 532 nm,
    wherein the absorber has a maximum absorbance in a range between 200 and 300 nm and an extinction coefficient at least 2 times larger than the polymer in the range, and
    wherein the absorber has a content of less than 0.1 to 0.001 wt % of the tube and the absorbance of the tube at 258 nm is at least 2 times the absorbance of the tube without the absorber.

13. A method of laser machining a substrate to form a stent, comprising:
    providing a tube comprising a mixture of a bioresorbable aliphatic polyester polymer and an absorber for increasing the amount of energy absorbed by the tube from a laser; and
    laser machining the polymer tube with a laser beam to form a scaffold, wherein the laser beam has a wavelength ($\lambda$) and a pulse width that provides multiphoton absorption of laser energy by the mixture at $\lambda/2$, wherein the absorber has a weight percent extinction coefficient at least 100 times greater than the polymer at $\lambda/2$, wherein the absorber content of the tube is sufficient to provide an absorbance of the tube at $\lambda/2$ at least 2 times the absorbance of the tube without the absorber, and wherein the absorber provides increased absorption of the laser energy by the tube and increased ablation of the tube resulting in faster laser cutting of the tube without an increase in power of the laser.

14. The method of claim 13, wherein the polymer is transparent to laser energy at $\lambda$.

15. The method of claim 13, wherein the absorber content of the tube is 0.1 to 0.001 wt %.

16. The method of claim 13, wherein the absorber is butylated hydroxytoluene (BHT) or methyl paraben.

17. The method of claim 13, wherein the polymer is poly(L-lactide).

* * * * *